United States Patent [19]

Linder

[11] 4,022,851

[45] May 10, 1977

[54] 1-HYDROXY-2-BROMO-3-ALLYLOXY-PROPANE PHOSPHORIC ACID ESTER

[75] Inventor: Seymour M. Linder, Baltimore, Md.

[73] Assignee: Alcolac Inc., Baltimore, Md.

[22] Filed: July 28, 1976

[21] Appl. No.: 709,253

[52] U.S. Cl. .......................... 260/950; 260/615 R; 260/978; 260/2 P

[51] Int. Cl.$^2$ ..................... C07F 9/32; C08F 130/2

[58] Field of Search ................................... 260/950

[56] References Cited

FOREIGN PATENTS OR APPLICATIONS 47-50092  7/1969  Japan ................................. 260/950

*Primary Examiner*—Anton H. Sutto
*Attorney, Agent, or Firm*—George L. Tone

[57] ABSTRACT

1-Hydroxy-2-Bromo-3-Allyloxypropane (allyl glycidyl ether bromohydrin) and 1-hydroxy-2-bromo-3-allyloxypropane phosphoric acid ester (allyl glycidyl ether bromophosphate), which are useful as polymerizable flame-retardants, are described. 1-Hydroxy-2-bromo-3-allyloxypropane was prepared by the reaction of equimolar amounts of allyl glycidyl ether and hydrobromic acid, in acetic acid, preferably at a temperature in the range of 25°–50° C. and the thus obtained allyl glycidyl ether bromohydrin was phosphated by reaction with a substantially equimolar amount of polyphosphoric acid, preferably at a temperature in the range of about 40°–50° C., to produce the 1-hydroxy-2-bromo-3-allyloxypropane phosphoric acid ester.

1 Claim, No Drawings

1-HYDROXY-2-BROMO-3-ALLYLOXY-PROPANE PHOSPHORIC ACID ESTER

The present invention relates to novel derivatives of allyl glycidyl ether; i.e. 1-hydroxy-2-bromo-3-allyloxy-propane (allyl glycidyl ether bromohydrin) and 1-hydroxy-2-bromo-3-allyloxypropane phosphoric acid ester (allyl glycidyl ether bromophosphate), which are of interest as polymerizable flame retardants.

I have discovered that the above novel derivatives of allyl glycidyl ether can readily be produced from allyl glycidyl ether in good yield and acceptable purity in the manner described in detail below, and that the products so produced, allyl glycidyl ether bromohydrin and allyl glycidyl ether bromophosphate, are useful as polymerizable flame retardants.

It is therefore an object of the present invention to provide certain new and useful chemical compounds; i.e., 1-hydroxy-2-bromo-3-allyloxypropane and 1-hydroxy-2-bromo-3-allylyoxypropane phosphoric acid ester.

It is a further object of this invention to provide a process for producing these novel compounds in good yield and acceptable purity.

Other and further objects will become apparent as the present description progresses.

In brief, in accordance with the preferred embodiment of the present invention; 1-hydroxy-2-bromo-3-allyloxypropane is produced by adding allyl glycidyl ether to a substantially equimolar amount of hydrobromic acid in acetic acid at a temperature ranging from ambient temperture to the boiling point of the reaction mixture, preferably at a temperature in the range of from about 25° C. to about 50° C. The thus obtained 1-hydroxy-2-bromo-3-allyloxypropane can be used as such as a polymerizable flame retardant, or it can be used as an intermediate and converted to the phosphate ester by phosphation, preferably by reaction with a substantially equimolar amount of polyphosphoric acid, of about 115% strength, at a temperature in the range of from ambient to about 100° C., preferably in the temperature range of about 40° C to about 50° C.

The details of the present invention may be most readily described by first considering the following specific examples of a preferred embodiment of the preferred method of making the novel compounds thereof:

EXAMPLE 1

1-Hydroxy-2-Bromo-3-Allyloxypropane

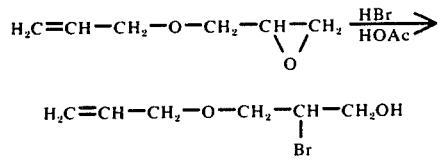

Eq. 1.

To a 5-liter, 4-neck flask, equipped with a thermometer, agitator and addition funnel, was charged 1690g. (10 moles) of 48% hydrobromic acid, and 1000 ml. of acetic acid. While agitating this mixture, 1140 g. (10 moles) of allyl glycidyl ether was added gradually, with cooling, over a period of several hours. When the addition was complete, the mixture was analyzed for free HBr and agitation was continued until analysis showed no free HBr, indicating that the reaction is complete. The temperature of the reaction mixture was maintained in the range of 25° C. to 50° C. throughout the reaction.

On completion of the reaction, the solvents (water and acetic acid) were then removed by vacuum stripping and the residual product, 1-hydroxy-2-bromo-3-allyloxypropane, recovered.

In several experiments, carried out in the manner described, the residual product was isolated in 80–90% yield and was 1-hydroxy-2-bromo-3-allyloxypropane of 90–95% purity as determined by analysis for organic bromine and unsaturation.

The residual product so recovered was of sufficient purity for use as a polymerizable flame retardant and for use as an intermediate for the production of 1-hydroxy-2-bromo-3-allyloxypropane phosphoric acid ester, as described in Example 2 which follows. However, it can be further purified by vacuum distillation if desired. Such vacuum distillation may be carried out in the presence of a minor amount, usually 0.1 to 0.3%, by weight, of a polymerization inhibitor such as hydroquinone, monomethyl ether of hydroquinone or 2,6- di-tert.-butyl-p-cresol (Ionol), if needed.

EXAMPLE 2

1-Hydroxy-2-Bromo-3-Allyloxypropane Phosphoric Acid Ester

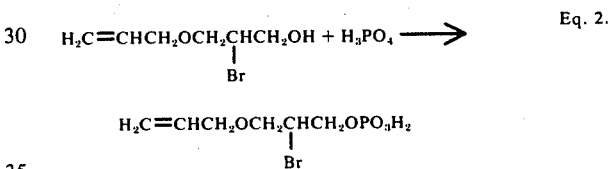

Eq. 2.

To a 2-liter, 4-neck flask, equipped with a thermometer, agitator and addition funnel, was charged 256 g. (3 moles) of 115% H$_3$PO$_4$. 622 g. (3 moles) of 94% 1-hydroxy-2-bromo-3-allyloxypropane was added over a period of 3–4 hours while agitating the reaction mixture and cooling to maintain the temperature in the range of 40°–50° C. On completion of the addition, agitation was continued until the unreacted phosphoric acid content became constant. The product so obtained, in several experiments carried out in the manner described, was 55–60% pure 1-hydroxy-2-bromo-3-allyloxypropane phosphoric acid ester (mono-ester) containing 8–13% unreacted phosphoric acid and unreacted 1-hydroxy-2-bromo-3-allyloxypropane, 21–31%. It was of acceptable purity for use as a polymerizable flame retardant; but could be purified, if desired, by vacuum distillation, in the presence if needed, of a minor amount, usually 0.1–0.3% by weight of a polymerization inhibitor such as hydroquinone, monomethyl ether of hydroquinone or 2,6- di-tert.-butyl-p-cresol.

It will be understood that the foregoing Examples are illustrative only of a preferred method of making the novel compounds of the present invention, and various changes which may be made therein will suggest themselves to those skilled in the art.

Thus in the reaction of allyl glycidyl ether with hydrobromic acid to produce allyl glycidyl ether bromohydrin illustrated in Example 1, the reaction temperature is not highly critical and the reaction may be carried out at any temperature ranging from ambient to the boiling point of the reaction mixture; the preferred temperature range is from about 25° to about 50° C. The addition time and rate of addition of the allyl glycidyl ether is not critical and will be largely dependent on the time required for heat removal to maintain the desired temperature of reaction. The reaction is usually complete within 15–60 minutes after the end of the allyl glycidyl ether addition.

In the phosphation reaction, illustrated in Example 2, reaction temperature is not highly critical and can range from ambient to about 100° C. The preferred temperature range is from about 40° to about 50° C; since at lower temperatures the reaction mixture may become too viscous to handle and at higher temperatures more darkening may occur. Similarly, reaction time is not critical and will largely depend upon the rate at which heat can be removed from the mixture to maintain the desired temperature of reaction. The reaction is usually complete within 30–20 minutes after the end of the allyl glycidyl ether bromohydrin addition.

As illustrated in Example 2, the preferred phosphating agent is polyphosphoric acid of 115% $H_3PO_4$ content, equivalent to about 83% of $P_2O_5$. The polyphosphoric acids commercially available range from 110–120% $H_3PO_4$, corresponding to about 80–86.5% $P_2O_5$, and may be used with substantially equivalent results. I prefer to use such polyphosphoric acids as the phosphating agent since they favor the production of the mono-ester, as illustrated in Eq. 2, and result in a product containing little if any di-ester,

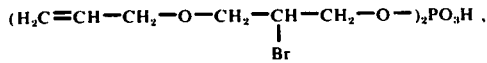

than either $P_2O_5$ alone, or 105% super-phosphoric acid; however, such latter phosphating agents may be used in situations where a higher diester content is not objectionable. The amount of free phosphoric acid remaining in the product generally ranges from 8–13%, as previously stated. This may be decreased by increasing the ratio of allyl glycidyl ether bromohydrin to polyphosphoric acid; while the amount of unreacted phosphoric acid in the product is thereby decreased, the amount of unreacted allyl glycidyl ether bromohydrin in the product is also increased. I, therefore, prefer to use substantially equimolar amounts of polyphosphoric acid and allyl glycidyl ether bromohydrin as illustrated in Example 2.

Since both the allyl glycidyl ether bromohydrin, obtained in Example 1, and the allyl glycidyl ether bromophosphate, obtained in Example 2, may be subjected, as such, to homopolymerization or copolymerization with other vinyl monomers to yield a new and useful class of polymers, there is no need to further purify them, as by fractional distillation under vacuum or vacuum stripping. In short the novel allyl glycidyl ether bromohydrin, of Example 1, and the novel allyl glycidyl ether bromophosphate, of Example 2, may be used as such in the preparation of homo- and co-polymers, in the preparation of flame-retardant latices and binders for woven and non-woven fabrics, in fibers to impart flame-retardant and anti-static properties and as flame retardant co-monomers in the preparation of vinyl and related co-polymers and other polymers as in the preparation of polyesters and in diallyl phthalate polymers.

Homopolymerization of the novel products of the present invention may be effected in solution in acetone by the use of a free radical polymerization catalyst such as di-tert.-butyl peroxide, benzoyl peroxide, lauroyl peroxide, methyl ethyl ketone peroxide, potassium persulfate and the like. The amount of catalyst added will vary, usually from 0.5–3.0% by weight of the monomer. Temperatures will vary over a considerable range but usually are in the range of 60°–200° C. The resulting homopolymers are tough, hard, fire-proof resins. The homopolymerization may be partial; i.e. by heating a solution of the novel polymerizable flame-retardant monomer in a polar solvent such as dioxane, acetone, etc., in the presence of the free radical polymerization catalyst, until a viscous solution is obtained, which may be applied as a coating to various surfaces and cured in ultra-violet light or in baking ovens to yield flame-resistant, tough hard resinous coatings. A viscous liquod partially homopolymerized product may also be obtained by controlling the period of heating, temperature and amount of polymerization catalyst employed.

The novel flame-retardant monomers of the present invention may also be co-polymerized with such co-monomers as vinyl acetate, vinyl chloride, styrene, acrylic and methacrylic acid esters, e.g. methyl or ethyl acrylate, methyl or ethyl methacrylate, hydroxyalkyl acrylates and methacrylates such as 2-hydroxy-ethyl acrylate or 2-hydroxyethyl methacrylate, diallyl phthalate etc. to yield a new class of polymeric products.

I claim:
1. A polymerizable flame-retardant monomer consisting essentially of 1-hydroxy-2-bromo-3-allyloxypropane phosphoric acid ester of the formula:

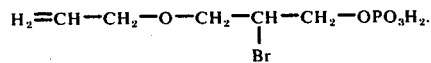

* * * * *

UNITED STATES PATENT AND TRADEMARK OFFICE
CERTIFICATE OF CORRECTION

PATENT NO. : 4,022,851
DATED : May 10, 1977
INVENTOR(S) : Seymour M. Linder

It is certified that error appears in the above-identified patent and that said Letters Patent are hereby corrected as shown below:

Column 3, line 18 : "30-20 minutes" should read ---30-120 minutes---

Signed and Sealed this thirtieth Day of August 1977

[SEAL]

Attest:

RUTH C. MASON
Attesting Officer

C. MARSHALL DANN
Commissioner of Patents and Trademarks